(12) United States Patent
Struckhoff et al.

(10) Patent No.: US 6,870,610 B1
(45) Date of Patent: Mar. 22, 2005

(54) METHOD AND APPARATUS FOR DETECTING DEFECTS IN A MATERIAL IN A LIQUID BATH

(75) Inventors: Andrew D. Struckhoff, Alexandria, VA (US); Eric S. Mosser, Alexandria, VA (US); William E. Shaw, Milan, MI (US)

(73) Assignee: DCS Corporation, Alexandria, VA (US)

( * ) Notice: Subject to any disclaimer, the term of this patent is extended or adjusted under 35 U.S.C. 154(b) by 156 days.

(21) Appl. No.: 10/139,365

(22) Filed: May 7, 2002

(51) Int. Cl.[7] ............................................. G01N 21/00
(52) U.S. Cl. .............................. 356/237.1; 356/238.3; 250/223 B
(58) Field of Search .................... 356/237.1–237.6, 356/336–343, 238.1–238.3, 239.1, 239.6; 382/108, 309; 250/223 B, 574, 575

(56) References Cited

U.S. PATENT DOCUMENTS

| | | | |
|---|---|---|---|
| 4,529,306 A | | 7/1985 | Kilham et al. |
| 4,802,762 A | | 2/1989 | Hill, Jr. |
| 4,904,080 A | * | 2/1990 | Afromowitz ................ 356/133 |
| 4,910,403 A | | 3/1990 | Kilham et al. |
| 5,187,765 A | | 2/1993 | Muehlemann et al. |
| 5,191,388 A | | 3/1993 | Kilham |
| 5,198,369 A | | 3/1993 | Itoh et al. |
| 5,239,358 A | | 8/1993 | Tokoyama |
| 5,255,089 A | | 10/1993 | Dybas et al. |
| 5,256,886 A | | 10/1993 | Wolf et al. |
| 5,383,776 A | | 1/1995 | Trail et al. |
| 5,465,052 A | * | 11/1995 | Henley ....................... 324/770 |
| 5,495,105 A | | 2/1996 | Nishimura et al. |
| 5,517,575 A | * | 5/1996 | Ladewski ................... 382/108 |
| 5,537,203 A | | 7/1996 | Carr |
| 5,694,221 A | * | 12/1997 | Knapp ........................ 356/427 |
| 5,786,894 A | | 7/1998 | Shields et al. |
| 6,542,849 B2 | * | 4/2003 | Sun ............................. 702/172 |
| 2000/0176617 | * | 11/2002 | Simonetti ................... 382/141 |

FOREIGN PATENT DOCUMENTS

GB     2 107 858     *  5/1983

* cited by examiner

Primary Examiner—Frank G. Font
Assistant Examiner—Sang Hoang Nguyen
(74) Attorney, Agent, or Firm—Shaw Pittman LLP

(57) ABSTRACT

A system and method for detecting defects in a material in a liquid bath, the system including a light that illuminates the material through the liquid bath, at least one camera with a view of the material through the liquid bath, and a digital processor in communication with the at least one camera. The at least one camera transmits image data to the digital processor and the digital processor analyzes the image data to identify defects in the material. In an embodiment of the invention, the system includes an anti-turbulence interface through which the at least one camera views the material.

43 Claims, 12 Drawing Sheets

METHOD AND APPARATUS FOR DETECTING DEFECTS IN A MATERIAL IN A LIQUID BATH

BACKGROUND

1. Field of the Invention

The present invention relates to a method and apparatus for material inspection, and more particularly, to a method and apparatus for detecting defects in transparent or translucent material moving through a liquid bath.

2. Background of the Invention

Inspection is an essential part of any process for manufacturing materials. Product manufacturers must ensure that the feedstock they use to manufacture their products meets or exceeds standards of quality, such as size, color, and purity. Inferior feedstock degrades the quality of the final product and reduces the manufacturer's sales and profits. Thus, to maintain strict product specifications and satisfied customers, manufacturers demand that the feedstock adhere to a minimum quality or grade.

Sensitive to such concerns, suppliers of raw materials routinely conduct inspections with objectives such as identifying and removing flawed material, assessing the overall quality of a batch of material, and separating a batch of material into portions of like size, color, purity, or grade. In addition, manufacturers must be able to determine, as early as possible in the process, whether the manufacturing equipment is producing flawed material. This early determination allows the manufacturer to take timely corrective action.

In the plastics industry, for example, manufacturers often shut down the extruders that produce the raw materials for routine maintenance. This maintenance procedure ensures that the extruder is always producing optimum product. Unfortunately, this maintenance procedure can be very time-consuming. If the maintenance procedure is conducted too frequently, valuable production time can be unnecessarily lost to maintenance time. The extruder production time can be maximized by automatically detecting the onset of flawed material in the manufacturing process, rather than relying on scheduled maintenance that may, in fact, be too frequent or too late.

When inspecting material, suppliers and manufacturers look for a variety of defects, depending upon the type of material. In food products, for example, defects include foreign matter, uncooked portions, unprocessed or clumped portions, and contaminants from pests such as insects or rodents. In plastic pellets, defects generally include foreign matter, charred raw material, contaminants from unmelted base constituents of the polymer material (often referred to as gels), incorrectly sized or colored pellets, broken pellets, and pellets that are stuck to each other. In addition, manufacturers sometimes measure the amount of fines (small chips or thread-like pieces that can break away from the pellets during manufacturing and transportation).

Traditionally, material inspection has been a slow, labor-intensive process limited to testing small samples instead of all material that is incorporated into the final product. Thus, theoretically, a sample might not be representative of the defects present in the rest of the material. In addition, although manufacturers would prefer to inspect material as it is being produced, in many instances this practice is not possible.

Although the following discussion of the traditional methods of inspection is in the context of the plastics industry, the methods and their associated drawbacks apply equally to other material inspections, such as inspections conducted during food processing. In the plastics industry, the current methods for inspecting raw plastic material include: 1) visual inspection of pellets by a person; 2) inspection of polymer ribbons formed from pellets; 3) inspection of molten polymer; and 4) automated inspection of the pellets. It is important to note that these methods are typically only suitable for base or raw materials that are transparent or translucent. Generally, however, this requirement is not a problem because coloring is usually added late in the manufacturing process.

Visual inspection of pellet material by a person is the most common method of material inspection. It is generally conducted in a quality control laboratory separate from the manufacturing process. The visual inspection method typically involves spreading a sample of particles on top of a light table (e.g., a glass or Plexiglas™ table with a light source below its top) or other white or light-colored surface, and examining each particle for a defect. If the size of a possible defect is small, the inspectors must strain their eyes to observe the defect or perhaps use a magnifying glass to focus on each particle. Although using the light table or light-colored surface enhances the defects, the process is only as reliable as the eyes and concentration of the human inspector. In addition to human error, using human inspectors increases labor costs and significantly reduces the speed at which material is analyzed. Visual inspection is therefore inappropriate for the in-line inspection of all material used in a process.

Inspection of polymer ribbons involves melting a sample of raw material pellets into a molten form, extruding the molten material into thin, ribbon-like shapes, and inspecting the ribbons for defects. The ribbon shapes are flatter than pellets, which eases handling and presents a larger viewable surface area This ribbon inspection technique can be incorporated into manual (visual inspection by a person) en and automated methods of inspection. Despite the advantages in handling and viewable surface area, the ribbon inspection technique suffers from the added time and expense of melting the raw material pellets. The equipment and manpower needed to accomplish this extra step add significantly to the overall cost of material inspection. Moreover, the extra steps involved in melting and extruding the material make this technique suitable only for evaluating small samples of process material and incompatible with the in-line inspection of all process material.

In addition to analyzing ribbons, some inspection techniques analyze the molten polymer itself, in a device known as a flow cell. The flow cell is a chamber with a conduit viewable through a window. U.S. Pat. No. 4,910,403 to Kilhamn et al. discloses a flow cell typically used for the molten polymer inspection technique. The molten polymer is channeled through the conduit, illuminated, and inspected as it passes under the window. This inspection technique can analyze the molten material either manually or with an automated device.

Although flow cell inspection techniques can identify defective portions of molten polymer, the techniques cannot separate those defective portions from the remaining acceptable portions. Thus, the method is suitable for grading the molten polymer or monitoring a manufacturing process for quality control, but not for removing defective portions and improving the quality of the molten polymer. In addition, the flow cell and the equipment necessary to convey the molten polymer introduce additional costs and complexities to the inspection process, and, because of their limited processing speed, are suitable only for spot-checking material. Indeed, Kilham et al. describes the inspection of only a portion of the fill volume of a polymer being manufactured. Thus, conventional flow cell inspection techniques are not optimal for inspecting all of the material moving through an extruder, While each of these methods offers a means to quantify defects in or grading polymer material through a sampling mechanism, none of these means offers a complete in-line inspection of all process materials.

SUMMARY OF THE INVENTION

The present invention is a system and method for automatically detecting defects in materials moving through a liquid bath. Unlike the devices of the prior at, the present invention can be incorporated into an in-line production process, and can inspect one hundred percent of the material used or produced by the process, such as all of the material exiting an extruder. Although described in the context of plastic manufacturing, the present invention could be used in any process that inspects a transparent or translucent material in a liquid bath for defects, such as with food products or glass products.

According to an embodiment of the present invention, the system for inspecting material in a liquid bath includes a light that illuminates the material through the liquid bath, at least one camera with a view of the material through the liquid bath, and a digital processor in communication with the at least one camera. The at least one camera transmits image data to the digital processor and the digital processor analyzes the image data to identify defects in the material.

In a further embodiment of the invention, the system includes an anti-turbulence interface through which the at least one camera views the material. The anti-turbulence interface has a surface in contact with the liquid of the bath to avoid the distortion caused by irregularities, such as ripples, on the surface of the bath.

Accordingly, an object of the present invention is to provide a method and apparatus for inspecting transparent, translucent, or opaque material that is conveyed through a bath.

Another object of the present invention is to provide an in-line material inspection process that analyzes all material used in a manufacturing process, identifies defective portions, and provides an indication when such defective portions are identified.

These and other objects of the present invention are described in greater detail in the detailed description of the invention, the appended drawings, and the claims.

DETAILED DESCRIPTION

Figure 1A:
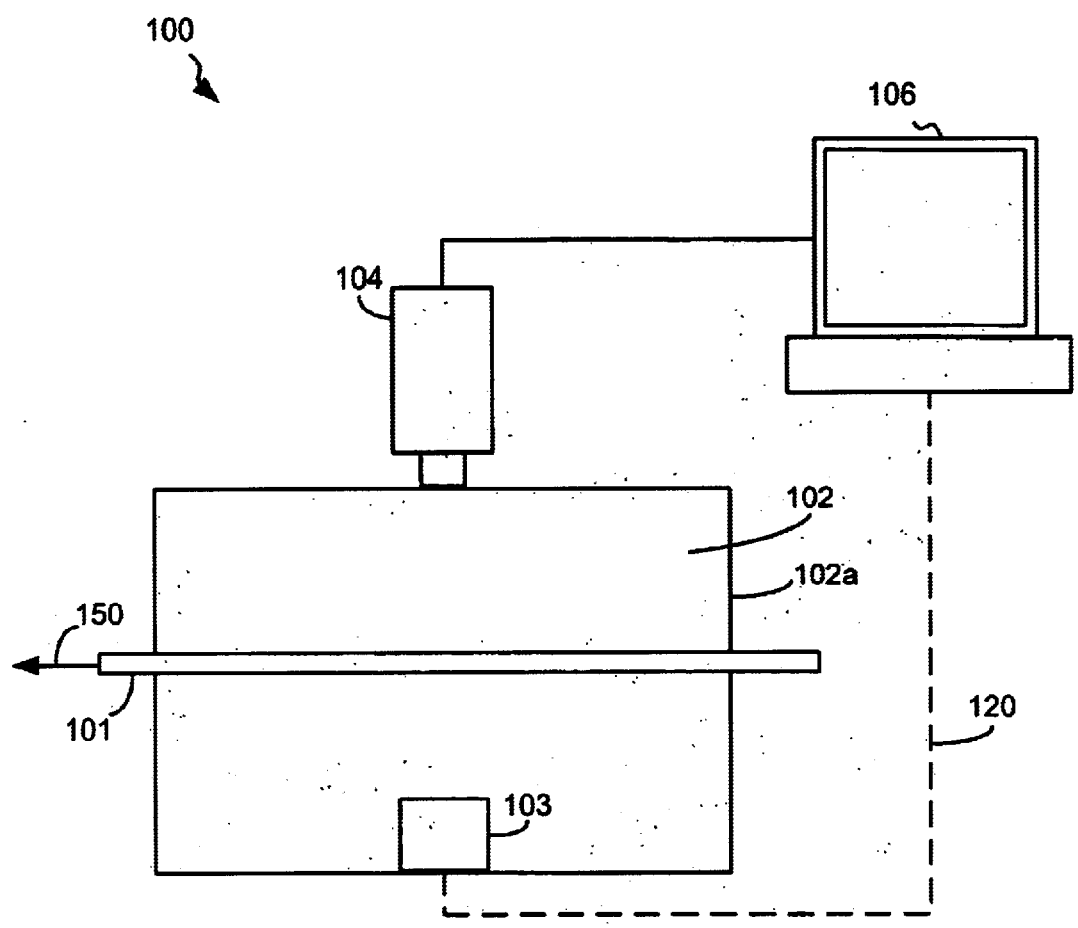
FIG. 1A is a schematic diagram of an exemplary system for inspecting material in a bath, according to an embodiment of the present invention.

FIG. 1A illustrates an exemplary system 100 for inspecting material 101 in a liquid bath 102, according to an embodiment of the present invention. FIG. 1A shows a top view of liquid bath 102. Material 101 may be, for example, an extruded raw material or a formed piece, which is run through a bath to cool the material or to control other features of the media. As an example, material 101 could be one or more polymer strands entering one side of bath 102 as molten polymer from an extruder, traveling in the direction of arrow 150, and exiting another side of bath 102 to enter a pelletizer that cuts the strand(s) into pellets. Notably, system 100 can monitor all of the polymer material produced by the extruder.

As shown, system 100 includes a light 103, at least one camera or imager 104, and a digital processor 106. Camera 104 is in communication with digital processor 106. Optionally, digital processor 106 is in communication with light 103 (discussed below). As material 101 travels through bath 102, light 103 illuminates material 101 through bath 102. Camera 104 views the illuminated material 101 through bath 102.

Digital processor 106 receives image data from camera 104, identifies defects in the image, and signals when defective material is detected.

Light 103 produces uniform diffuse light that illuminates material 101. Light 103 is positioned at a location proximate to material 101 that provides enough illumination for camera 104 to detect an image of material 101. In an embodiment of the present invention, light 103 is positioned such that material 101 passes in between light 103 and camera 104, so that material 101 is fully backlit in front of camera 104.

Light 103 can be submerged in bath 102, as shown in FIG. 1A, or can be located adjacent to bath 102 providing illumination through, for example, a transparent wall of the structure (e.g., tank) that holds bath 102. Of course, if light 103 is submerged in bath 102, light 103 would include a liquid-tight enclosure that isolates electrical components from bath 102.

Figure 1B:
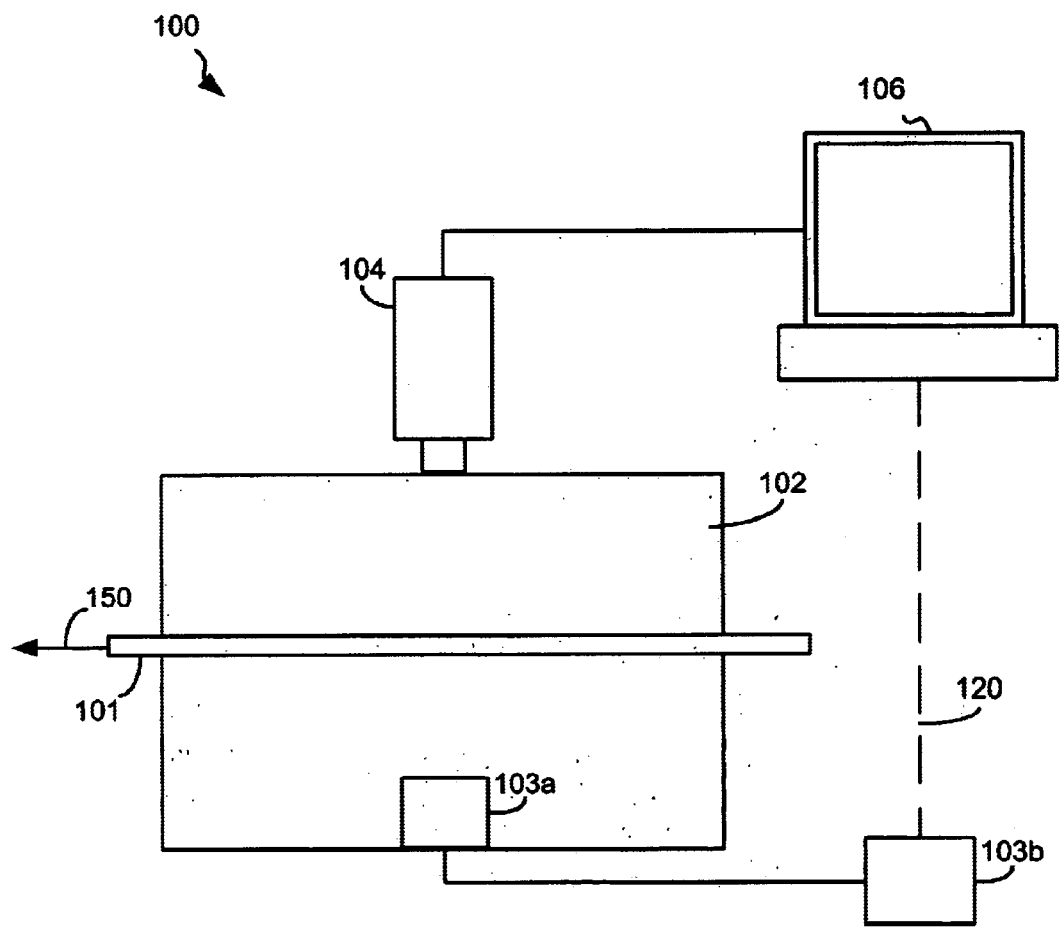
FIG. 1B is a schematic diagram of the system of FIG. 1A, with the light including a light diffuser in the bath and a light source outside of the bath, according to an embodiment of the present invention.

In another embodiment, light 103 includes a submersible light diffuser located inside bath 102, which is connected by fiber optic cables to a light source located outside of bath 102. FIG. 1B shows this embodiment, in which light 103 includes a light diffuser 103a and a light source 103b. Light diffuser 103a is a liquid-tight submersible fiber-optic converter that receives light transmissions from light source 103b. Light source 103b is located outside of liquid bath 102 to keep its electrical components isolated from bath 102.

The illumination from light source 103b is optically communicated to one end of the fiber-optic converter of light diffuser 103a. The submersible fiber optic converter directs the illumination from light source 103b via optical fiber to the light diffuser 103a, where the illumination is then spread over a wide area. The converter can also contain a glass or plastic plate to add additional diffusion to the illumination. In this manner, light 103 supplies a uniform diffuse light that creates a uniform background signal out of which to identify defects.

Returning to FIG. 1A, in an embodiment of the present invention, light 103 includes a lamp controller that houses a lamp or light bulb. Light 103 could also be multiple lamp controllers, depending on the amount of light required to inspect a given material. In a specific implementation, light 103 includes a stabilized halogen lamp controller. The lamp controller is stabilized to accurately maintain a preset light level for an extended duration, as opposed to unstabilized lamp sources, which provide less accuracy. In the embodiment of FIG. 1B, the lamp controller would be included in light source 103b.

The uniform light produced by light 103 enables a more accurate detection of defects by evenly illuminating material 101. In addition to providing this uniform light, light 103 is also preferably positioned a short distance away from material 101, to limit the degree to which light rays from light 103 bend as they travel through the strands of material 101. Light 103 is preferably positioned as close as possible to material 101 without hindering the movement of material 101 through bath 102. As the distance between the strands of material 101 and light 103 increases, the edges of the strands tend to darken. The dark edges can either hide defects or cause digital processor 106 to signal false defects. Of course, in reaching an appropriate compromise between an acceptable amount of shading and the detection of a defect, digital processor 106 can be calibrated to tolerate a threshold amount of shading or dark edges, without signaling the presence of a defect (discussed below).

Camera 104 captures images of material 101 as material 101 passes through bath 102. According to an embodiment of the present invention, the lens of camera 104 is adjusted to focus on material 101, which is located between light 103 and camera 104. Preferably, camera 104 views material 101 through bath 102 at a constant optical path length, free from any distortion attributable to the liquid of bath 102. Thus, in FIG. 1A, camera 104 views material 101 through, for example, a transparent wall, panel, or window of structure 102a (e.g., tank) containing the liquid bath 102. Although FIG. 1A shows camera 104 abutting the structure that holds bath 102, camera 104 could be set back from the structure with a space between camera 104 and the structure. In addition, camera 104 can be positioned at any number of locations in or around bath 102 so long as camera 104 is able to capture image data of material 101 that is sufficient for digital processor 106 to detect defects. For example, camera 104 could be positioned over the surface of bath 102 as discussed in detail below.

Although camera 104 could be of any type, including traditional video cameras, in an embodiment of the present invention, camera 104 is a line scan camera that acquires consecutive one-dimensional scans across the moving material 101 as material 101 travels through the viewing field of camera 104. Line scan cameras are preferable to traditional video cameras because of their speed of operation and because they only require illumination of the one-dimensional area across material 101 that correlates to the area viewed by the camera.

If other camera types are used, as one of ordinary skill in the art would appreciate, the design of light 103 would be adapted accordingly. For example, if camera 104 has a two-dimensional field of view, as opposed to a one-dimensional line scan camera, then light 103 would be adapted to fully illuminate the entire two-dimensional field of view. Thus, for example, light 103 could include an array of lamps across the field of view.

By illuminating material 101 with light from the visible spectrum, camera 104 can record images that show varying degrees of darkness between normal material and defective material. Defects such as charred material and foreign matter appear as dark sections of the material image. Defects related to gels in material 101 would likely not be detected with the light from the visible spectrum, however. Thus, as would be apparent to one skilled in the art, alternative embodiments of the present invention use different types of light to detect gels within material 101. For example, light 103 could produce ultraviolet light, which would cause a gel defect to fluoresce. Using filters, camera 104 could detect this fluorescence in the visible spectrum.

Figure 2:
FIG. 2 is an image of an exemplary defect embedded in a polymer strand, according to an embodiment of the present invention.

Digital processor 106 is, for example, a computer that receives the image information captured by camera 104 and analyzes the image information for defects. In an embodiment of the present invention, digital processor 106 includes a signal-conditioning module that serves as the frame grabber of system 100 and conditions signals to and from camera 104. If camera 104 is a line scan camera, then digital processor 106 stores data from the one-dimensional line scans of camera 104 in a memory buffer, assembles the line scan data into two-dimensional arrays, and looks for dark portions indicative of a defect. FIG. 2 illustrates an exemplary two-dimensional image 200 of a defect embedded in a polymer strand. The defect appears in circle 202. If digital processor 106 finds a defect in a strand, digital processor 106 issues a signal.

Digital processor 106 can be an individual component of the present invention or can be integrated with camera 104 in a single device. In this specification and in the claims, the term "computer" means a portion of a computer with software, a microprocessor programmed according to this invention, a single computer with software, or one or more computers with software in communication with each other.

In an alternative embodiment of the present invention, digital processor 106 is in communication with light source 103 as represented, for example, by the dotted line 120 in FIGS. 1A and 1B. In this manner, digital processor 106 can control the degree of illumination provided by light 103, for purposes of optimizing the image received by camera 104. Thus, as digital processor 106 receives image data from camera 104, digital processor 106 can evaluate the image data, determine what light adjustments are required to improve the image data, and can invoke the appropriate light adjustments through communication link 120.

Figure 1C:
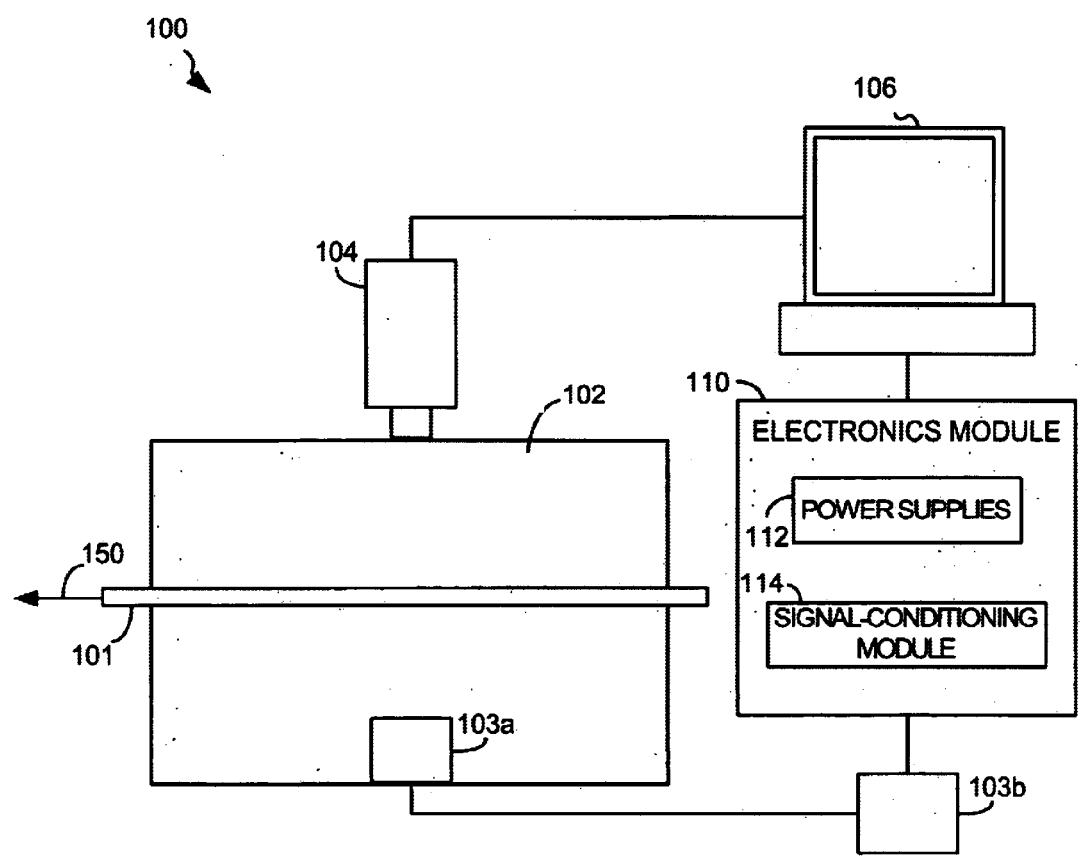
FIG. 1C is a schematic diagram of the system of FIG. 1B, in which the system has an electronic control module in communication with the digital processor and the light source, according to an embodiment of the present invention.

In a specific implementation of this alternative embodiment, FIG. 1C shows system 100 having an electronics module 110 in communication with digital processor 106 and light source 103b. Electronics module 110 contains power supplies 112 for the system 100. Electronics module 110 also acts as a common junction box for computer-generated signals, and can include wiring for lamp indicators and other electrical components. A main power supply in electronics module 110 provides power for camera 104. Other auxiliary power supplies could be included in electronics module 110 as well. Electronics module 110 also contains a signal-conditioning module 114, which buffers digital status signals to and from digital processor 106.

Digital processor 106 is able to control the light produced by light source 103b. In this manner, digital processor 106 can analyze the image data received from camera 104 and adjust the light produced by light source 103b to optimize the image data. Digital processor 106 can communicate directly with light source 103b, or optionally through electronics module 110.

Figure 3:
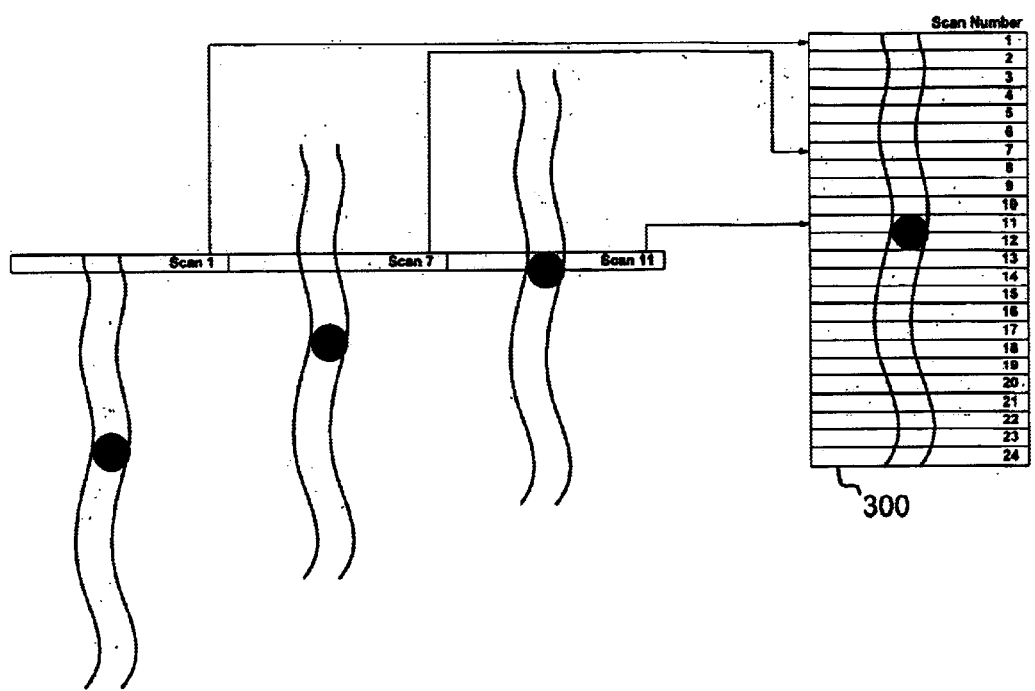
FIG. 3 is a schematic representation of the recording of one-dimensional lines and the assembling of the lines into a two-dimensional image, according to an embodiment of the present invention.

FIG. 3 schematically illustrates an exemplary recording of twenty-four one-dimensional lines, 1 through 24, and the assembling of the lines into a two-dimensional image 300. In the first portion of image 300, line number 1 is recorded. Following a specified time interval, line number 2 is recorded. In between the recording of lines 1 and 2, the material has moved an incremental amount. The individual recordings of lines 1, 7, and 11 are shown for illustrative purposes, though the recording of all lines is performed in sequence. The two-dimensional array 300 captures the complete image of material 101, including any defects (e.g., as shown in lines 11 and 12 of image 300).

Figure 1D:
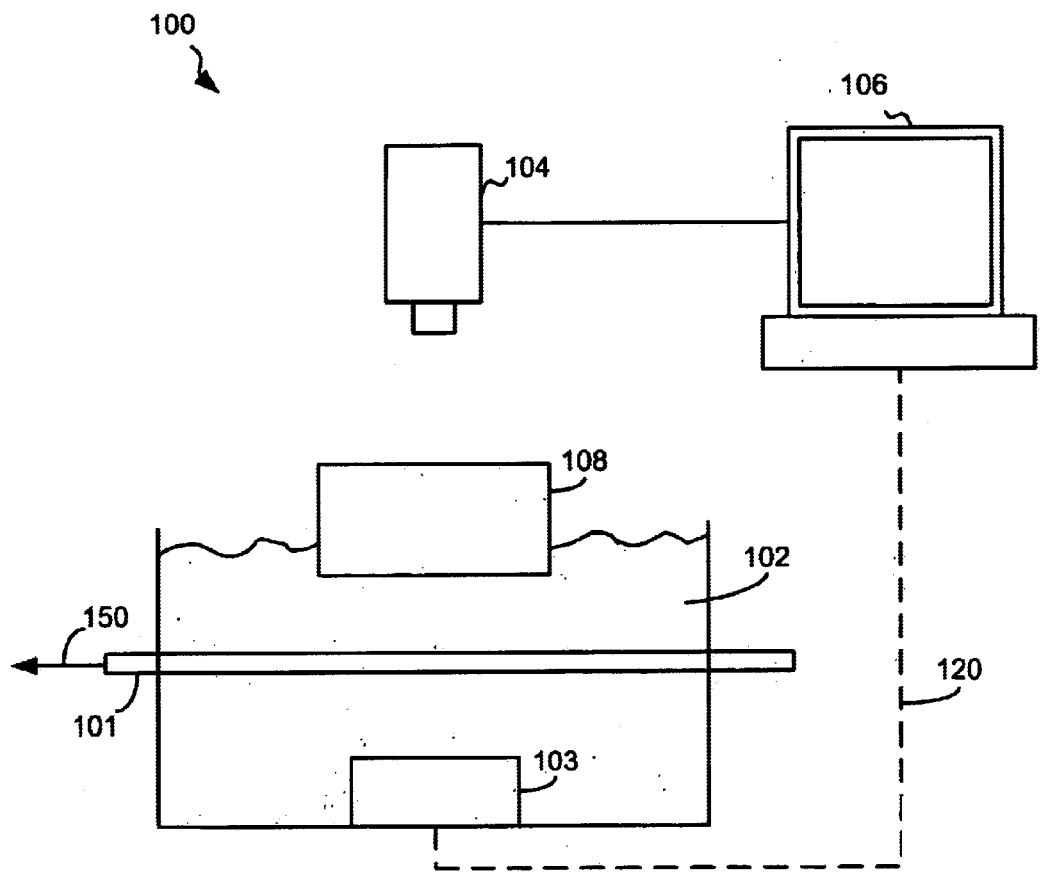
FIG. 1D is a schematic diagram of an exemplary apparatus for inspecting material in a bath, in which the camera faces the top surface of the liquid bath and views the material through an ant-turbulence interface, according to an embodiment of the present invention.
Figure 1E:
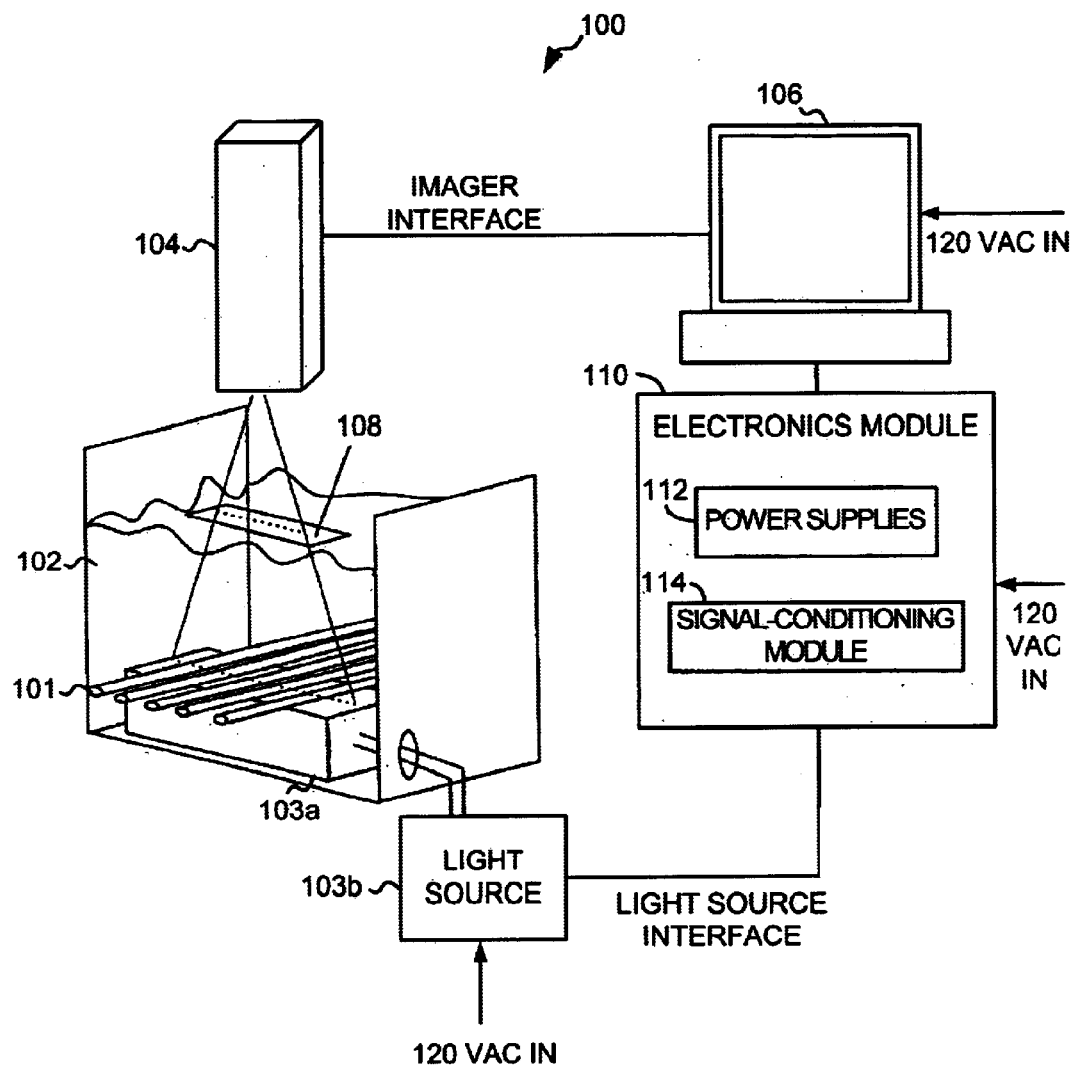
FIG. 1E is a schematic diagram of the exemplary apparatus of FIG. 1D, with the light including a submersible light diffuser connected by fiber optic cables to a light source, according to an embodiment of the present invention.

In a further embodiment of the present invention, camera 104 is located above bath 102, outside of bath 102, and with a view of the surface of bath 102. In this configuration, ideally, the surface of liquid bath 102 would be flat to maintain a constant optical path length between camera 104 and material 101 without distortion. However, in practical implementations, it is difficult to keep the surface of bath 102 still as material 101 travels through bath 102. Thus, in a further embodiment of the present invention, as shown in FIGS. 1D and 1E, system 100 includes an anti-turbulence interface 108, which avoids camera 104's viewing material 101 through ripples or other irregularities at the surface of liquid bath 102 (which is shown in FIGS. 1D and 1E from a side view). These irregularities in the surface of liquid bath 102 can cause variations in the signal received by camera 104, which can be interpreted as defective material.

In an exemplary implementation, anti-turbulence interface 108 is positioned above light 103, and contains a transparent view surface at its bottom through which camera 104 views material 101 over light 103. The view surface can be made of, for example, glass or plastic. Anti-turbulence interface 108 is positioned so that its lower view surface is at or below the waterline of bath 102, such that the lower view surface is wetted. In this manner, the view surface is below any turbulence on the surface of bath 102 that might distort the image received by camera 104.

Figure 4:
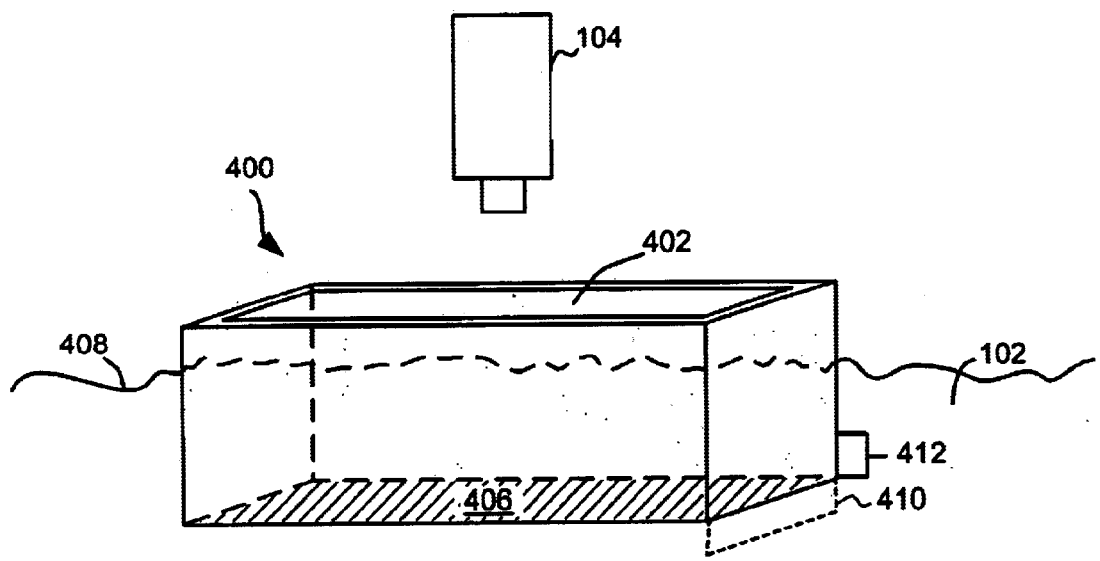
FIG. 4 is a schematic diagram of an exemplary anti-turbulence interface, according to an embodiment of the present invention.

FIG. 4 illustrates an exemplary anti-turbulence interface 400. As shown, anti-turbulence interface 400 is a five-sided box with its open side 402 facing up toward camera 104. Opposite the open side 402, anti-turbulence interface 400 has a transparent bottom face 406. Bottom face 406 is in contact with the liquid of bath 102 at or below the surface 408 of bath 102. Thus, ripples or other turbulence on surface 408 do not interfere with the view through bottom face 406.

In a further embodiment of the present invention, the anti-turbulence interface inhibits bubbles from collecting on its bottom view surface. Similar to the collection of carbon dioxide bubbles on the inside of a glass filled with champagne, small molecules of oxygen (or other gas) that are suspended in the liquid of bath 102 may collect on the bottom view surface of the anti-turbulence interface. As these molecules accumulate on the anti-turbulence interface, they form bubbles that act like lenses on the interface, causing noise in the signal (e.g., dark spots). If the bubbles become too large, they can cause a signal that looks like a defect, resulting in a false alarm.

Figure 5:
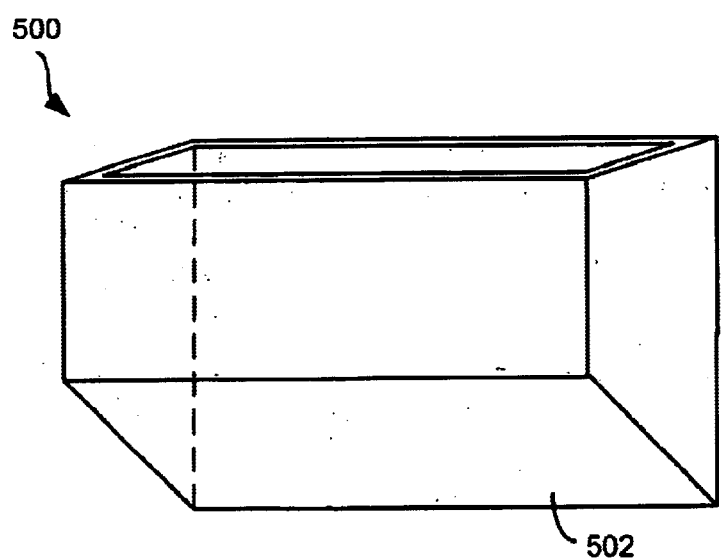
FIG. 5 is a schematic diagram of an exemplary anti-turbulence interface having an angled bottom surface, according to an embodiment of the present invention.

Thus, to inhibit the collection of bubbles, an embodiment of the anti-turbulence interface includes an angled bottom view surface (with respect to the general horizontal plane of the surface of the liquid bath), such as is shown on the anti-turbulence interface 500 of FIG. 5. Angling the bottom view surface 502 reduces the possibility of bubbles becoming trapped under anti-turbulence interface 500. In this example, anti-turbulence interface 500 is a five-sided box with a transparent bottom view surface 502, similar to that of FIG. 4, except that the bottom surface 502 of anti-turbulence interface 500 is angled to discourage bubbles from collecting on surface 502.

In a further embodiment, the bottom view surface of the anti-turbulence interface is coated with a material that inhibits gas molecules from sticking and collecting on the view surface. For example, the bottom view surface could be coated with a transparent hydrophilic material that attracts the liquid of bath 102, promotes a fill wetting of the bottom view surface, and thereby inhibits bubbles from forming between the liquid and the bottom view surface.

Figure 6:
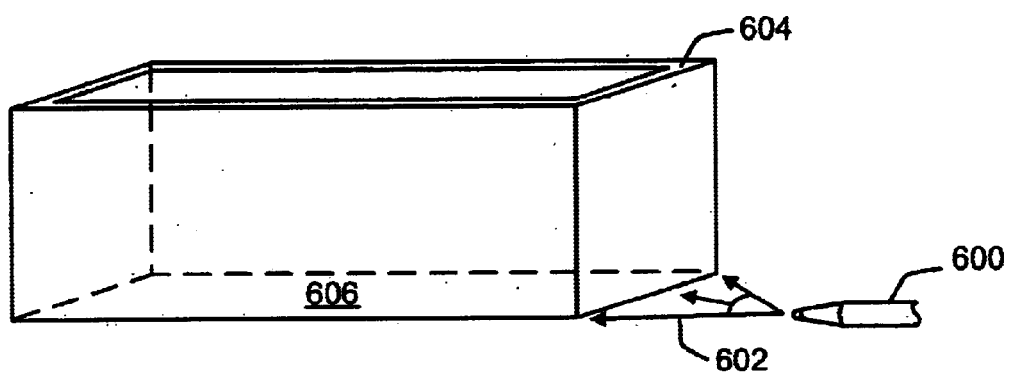
FIG. 6 is a schematic diagram of an exemplary means for removing bubbles from an anti-turbulence interface, according to an embodiment of the present invention.

If bubbles do form on the anti-turbulence interface, a further embodiment of the anti-turbulence interface includes means for removing the bubbles. This means for removing bubbles could be, for example, a mechanical device 410 (shown in FIG. 4) that sweeps the interface (e.g., a squeegee arm), a vibration mechanism 412 (shown in FIG. 4) that vibrates the interface to break the bubbles free, or an injection-mechanism that directs a flow of the liquid of bath 102 across the interface to remove the bubbles (e.g., a positive jet of fluid or a channel of fluid). FIG. 6 illustrates an exemplary injection mechanism 600 that provides a fan-shaped jet of fluid 602 across the bottom view surface 606 of an anti-turbulence interface 604.

Figure 1F:
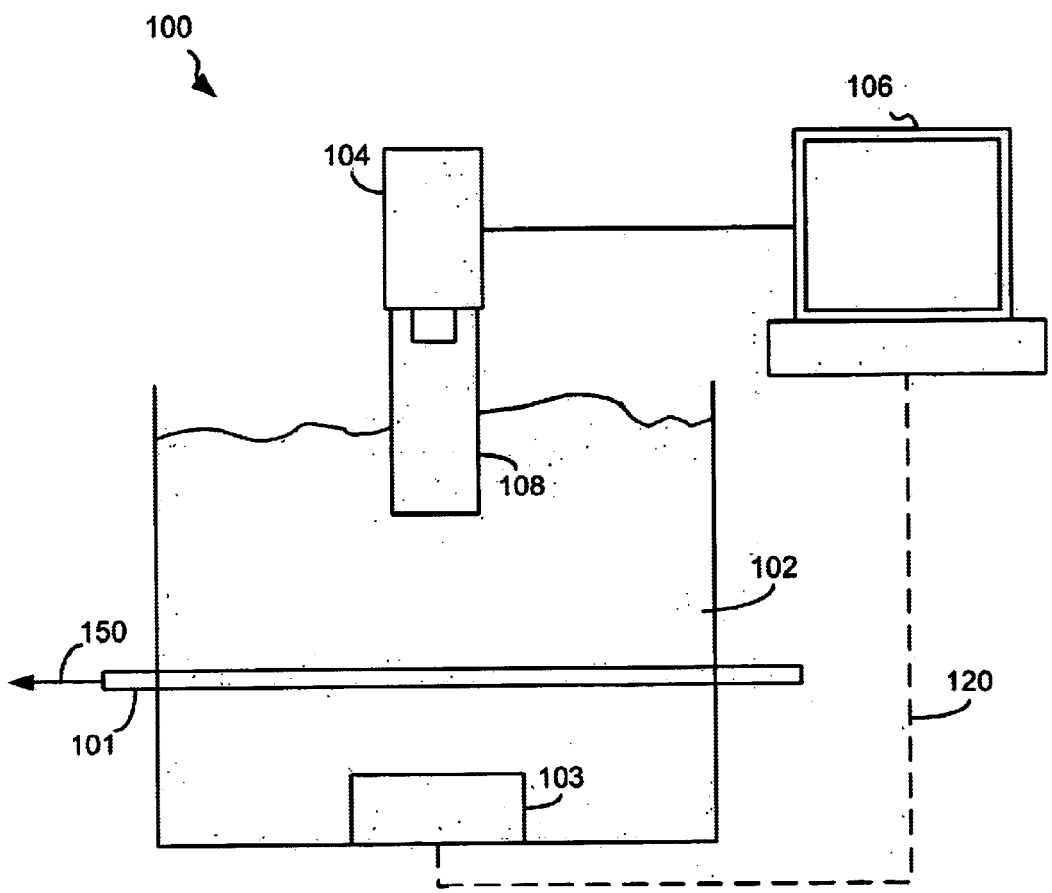
FIG. 1F is a schematic diagram of an exemplary apparatus for inspecting material in a bath, in which an anti-turbulence interface is attached to the camera, according to an embodiment of the present invention.

In an alternative embodiment of the system 100 of FIGS. 1D and 1E, camera 104 and anti-turbulence interface 108 are attached to each other, as shown in FIG. 1F. For example, anti-turbulence interface 108 could be a tube mounted over the lens of camera 104. The tube would have a clear bottom surface. In this manner, camera 104 would be lowered toward bath 102 (shown from a side view in FIG. 1F) until the anti-turbulence interface 108 attached to camera 104 touches or breaks the surface of the liquid bath 102. In this configuration, anti-turbulence interface 108 provides all of the functions described above for a separate anti-turbulence interface that is not attached to camera 104. In addition, the anti-turbulence interface 108 of FIG. 1F (which is attached to camera 104) could be adapted to inhibit or remove bubbles from collecting on its bottom surface, as described above in reference to FIGS. 4–6.

Figure 1G:
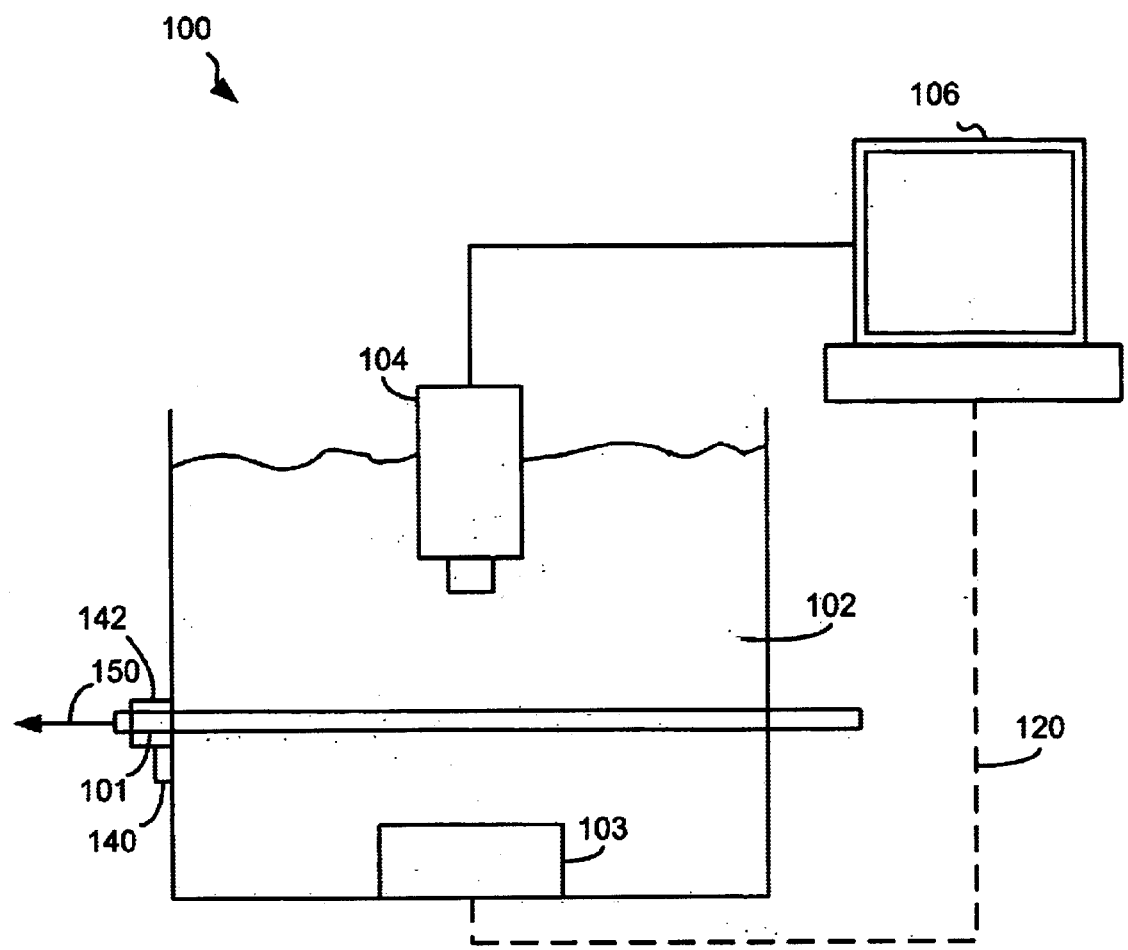
FIG. 1G is a schematic diagram of an exemplary apparatus for inspecting material in a bath, in which the camera is at least partially submerged in the bath, according to an embodiment of the present invention.

In a further embodiment of the present invention, FIG. 1G illustrates a configuration of system 100 in which camera 104 is submerged in liquid bath 102. By submerging camera 104 in bath 102, this embodiment avoids the need for an anti-turbulence interface or transparent panel for viewing material 101 through bath 102. Submerging camera 104 therefore ensures that camera 104 has a constant optical path length and avoids the image distortion caused by viewing material 101 through surface irregularities of liquid bath 102. Camera 104 can be partially submersible, as shown in FIG. 1G, or can be fully submersible, depending on the particular type of camera. As shown in FIG. 1G, at least a portion of camera 104 is sealed to prevent the liquid of bath 102 from harming the mechanical and electrical components of camera 104. As an example, the submersible two-dimensional framing video camera, model MVC2000-WP-LED, produced by Micro Video Products, of Ontario, Canada, could serve as camera 104 of FIG. 1G. Of course, submersible line-scan cameras could be used as well.

Referring to FIG. 1A, a specific implementation of system 100 operates according to the following exemplary method. In this example, material 101 is one or more polymer strands. Molten polymer exits an extruder on one side of bath 102, enters bath 102, and starts to cool and harden into polymer strands. To initiate the flow of the polymer material 101, an operator grabs the cooled strands from under the extruder just below the surface of bath 102, and pulls the strands through bath 102 to an opposite side of bath 102. The operator pulls the strands out of bath 102 and feeds them into a pelletizer that cuts the strands into pellets. After the strands are fed into the pelletizer, the extruder and the pelletizer together convey material 101 through bath 102, ie., the extruder pushes material 101 in a molten form into bath 102 and the pelletizer pulls material 101 in a hardened form out of bath 102. With the material 101 moving, camera 104 then views material 101 and relays image data to digital processor 106 for the detection of defects, as discussed above.

In some extruding processes, conveyors belts move material 101 from one end of bath 102 to the other. The strands of material 101 lay on top of the conveyor belts. For these applications, an embodiment of the present invention positions camera 104 and light 103 at a point in between two conveyor belts, where the strands span the conveyor belts and can be illuminated and viewed without obstruction.

In initiating the flow of material 101 through bath 102 by grabbing and pulling the strands across bath 102, an operator must have a certain degree of unobstructed access to bath 102. In one implementation, the bath is seven feet long and eight inches deep. Thus, it is preferable for the operator to be able to pull the strands through the long, shallow bath without being hindered by the components of system 100. In addition, to maintain a constant optical path length between camera 104 and material 101, it is preferable that camera 104 be secured at a fixed location that does not limit the operator's access to bath 102. Accordingly, an embodiment of the present invention mounts camera 104 at a fixed location outside of bath 102 and out of the way of the operator. In the configuration of FIG. 1A, camera 104 would be spaced an adequate distance from the side of the structure containing bath 102. In the configuration of FIG. 1D, camera would be positioned above bath 102 high enough for the operator to reach in bath 102 without hitting camera 104.

As a further embodiment of FIG. 1D, which provides even more convenient access, anti-turbulence interface 108 is readily removable and replaceable. For example, anti-turbulence interface 108 is mounted on an arm that swings in and out of bath 102. In this manner, the machine operator can swing anti-turbulence interface 108 out of the way, feed material 101 through bath 102, and swing interface 108 back into place after material 101 is being conveyed through bath 102. In a further embodiment, removable anti-turbulence interface 108 is coupled to a switch that triggers system 100 to begin inspecting material 101 whenever interface 108 is in position over bath 102.

In addition to easing operator access, positioning camera 104 at a distance from bath 102 can offer other benefits. First, because camera 104 does not have to be submersible or waterproof, the cost of camera 104 is minimized. Second, for safety considerations, the electrical components of camera 104 can be isolated from the liquid bath 102. Third, camera 104 can be permanently fixed to maintain a constant optical path length to material 101, without having to move camera 104 to give an operator access to bath 102. Finally, the greater distance between camera 104 and material 101 enables a more favorable, wider view of material 101, especially in comparison to a camera that is submerged in a shallow bath, which necessitates a lens with a short focal length. Such a lens can introduce distortion problems at the periphery of the view area.

After the inspection is initiated, system 100 inspects one hundred percent of material 101 for defects, identifies defective material, and transmits a signal indicating that a defective material has been observed. In a further embodiment of the present invention, this signal triggers a further function. For example, the signal could activate an alarm to alert an operator that defective material has been detected. As another example, the signal could trigger a separation mechanism that separates the defective material from the good material. As another example, the signal could notify an external control system 140 (as shown in FIG. 1G) of the presence of the defective material, and in response, the control system could then perform any number of actions based on the notification (e.g., marking the batch in which the defect was detected).

In a specific implementation of system 100 in which polymer strands are cut into pellets, the defect signal from digital processor 106 triggers a separation mechanism 142 (shown in FIG. 1G) that is positioned downstream of system 100 in the production sequence. For example, after the strands (material 101) move through bath 102, they enter a pelletizer, which cuts the strands into pellets. The pellets are then routed to a packaging area where they are placed in shipping containers. Based on the rate of production, a pellet exits the pelletizer after a predetermined duration following the inspection by system 100 of the portion of the strand corresponding to the pellet. Thus, upon detection of a defect in a strand, the separation mechanism would activate after the pre-determined duration to remove the defective pellet corresponding to the defective portion of the strand.

The separation mechanism could be, for example, a mechanical valve or pneumatic jet that redirects the defective pellet away from the flow of non-defective pellets leading to the shipping container. The separation mechanism would be precise enough to reject only the specific defective pellet in the stream of pellets. For example, the separation mechanism could be a pneumatic jet that delivers a short blast of air that redirects a pellet into a reject conduit, which would lead to a reject pellet bin that collects the defective pellets.

According to an embodiment of the present invention, digital processor 106 preferably accounts for the speed (e.g., inches per second) at which material 101 moves through bath 102. This speed could be an assumption based on the overall production speed of the manufacturing process into which system 100 is incorporated.

Preferably, however, an embodiment of the present invention provides digital processor 106 with a periodically updated value for the speed of material 101. For example, digital processor 106 could be in communication with a production machine, such as an extruder or pelletizer, that reports its feed rate to digital processor 106. As another example, digital processor 106 could be in communication with one or more sensors, such as laser Doppler sensors, that measure the speed of material 101.

Having the material speed, digital processor 106 can correctly interpret the images of camera 104. For example, in the case of a line scan camera, digital processor 104 can correctly assemble the individual line scans into a two-dimensional image. Having an accurate measure of speed also enables digital processor 106 to precisely activate a separation mechanism so that when digital processor 106 detects a defect, it sends a signal to the separation mechanism at the exact time that the defective material reaches the separation mechanism.

In any of the above embodiments, the method by which digital processor 106 identifies defects preferably involves a calibration step using camera 104. This calibration minimizes variations in the camera gray levels across the camera field of view. Light 103 can have local variations ranging from 5% to 10% of the average. The calibration involves collecting image data when material 101 is not flowing through system 100 and calculating, pixel by pixel, a correction factor required to eliminate the observed variations across the camera field of view.

In addition to light correction, calibration can involve determining the pixel size at the inspection site. This determination is generally a one-time calibration. A known distance standard is placed at the location of material 101. The lens of camera 104 images this standard onto a photodiode array. By counting the number of pixels over which the standard extends, the pixel resolution can be determined.

The method by which digital processor 106 identifies defects can also involve the setting of a system threshold. The threshold can be set either automatically or manually. The objective in setting the threshold for digital processor 106 is to distinguish between the video level associated with acceptable material and the video level associated with a defect contained in the material. The threshold represents a video level that is too low to be considered a non-defective material video level and is low enough to be considered a defective material video level. Thus, the setting of the threshold is largely a balancing between missing minor defects and triggering false positives because the threshold level is too close to the non-defective material video level.

Figure 7:
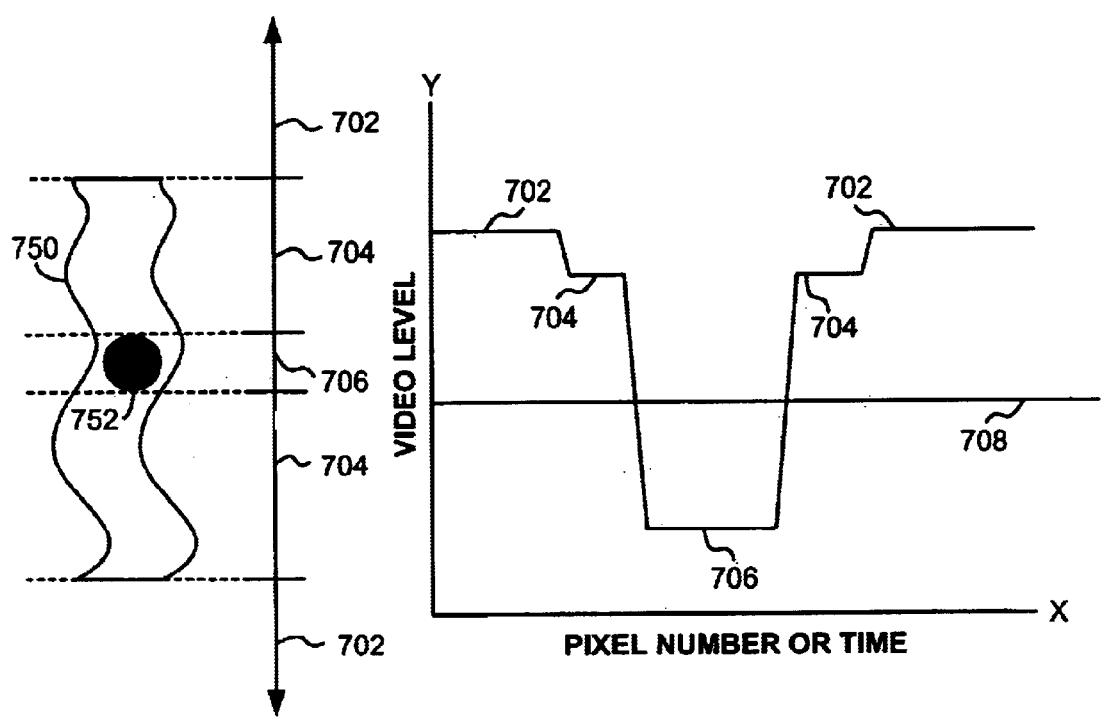
FIG. 7 is an image showing the relative comparison between different camera video levels in an exemplary system for inspecting material in a liquid bath, according to an embodiment of the present invention.

FIG. 7 shows a relative comparison between different camera video levels in an exemplary system for inspecting material in a liquid bath, according to an embodiment of the present invention. The graph of FIG. 7 plots video level (y-axis) as a function of pixel number or time (x-axis). The pixel numbers correspond to consecutive pixels in a line scan, while the video level corresponds to the lightness or darkness of the line scan image. For the video level, the lower the value is, the darker the image appears.

As shown in the graph and in the schematic representation of scans of a strand 750, the background level 702 is typically the highest video level and corresponds to the times at which no material is viewed by camera 104. The non-defective material video level 704 is generally somewhat below the background level 702, and corresponds to the times at which non-defective material is viewed by camera 104. The defective material video level 706 is substantially below the level 704 for non-defective material, and corresponds to the times at which defective material 752 is viewed by camera 104. A threshold 708 is set between the non-defective material video level 704 and the defective material video level 706 to distinguish between non-defective and defective material, and to indicate a defect accordingly.

Using the threshold level 708, digital processor 106 looks only for the presence of defects and does not track the edges of the material. Thus, the present invention offers the advantage of being able to accommodate any number of strands or any shape of material to be passed under camera 104.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A system for identifying defects in material traveling through a liquid bath comprising:
   (a) a light that illuminates the material through the liquid bath;
   (b) at least one camera with a view of the material through the liquid bath; and
   (c) a digital processor in communication with the at least one camera,
      wherein the at least one camera transmits image data to the digital processor and the digital processor analyzes the image data to identify defects in the material, and wherein the digital processor is in communication with the light and is adapted to control the degree of illumination provided by the light to optimize the image data.

2. The system of claim 1, wherein the material passes through the bath in between the at least one camera and the light.

3. The system of claim 1, wherein the at least one camera and the digital processor are an integrated device.

4. The system of claim 1, wherein the light is submerged in the liquid bath.

5. The system of claim 1, wherein the light comprises a light diffuser in the liquid bath in optical communication with a light source outside of the liquid bath.

6. The system of claim 1, wherein the light produces one of ultraviolet light and visible light.

7. The system of claim 1, wherein the at least one camera is submerged in the liquid bath.

8. The system of claim 1, wherein the at least one camera is outside of the liquid bath, and wherein the system further comprises an anti-turbulence interface having a surface in contact with the liquid bath, wherein the at least one camera views the material through the surface.

9. The system of claim 8, wherein the anti-turbulence interface is attached to the at least one camera.

10. The system of claim 8, wherein the surface of the anti-turbulence interface is angled with respect to the general horizontal plane of the surface of the liquid bath.

11. The system of claim 8, wherein the surface of the anti-turbulence interface is coated with a material that inhibits collection of gas molecules on the surface.

12. The system of claim 8, further comprising a liquid injection mechanism that produces a flow of liquid across the surface of the anti-turbulence interface to remove bubbles from the surface of the anti-turbulence interface.

13. The system of claim 8, further comprising a vibration mechanism that vibrates the anti-turbulence interface to remove bubbles from the surface of the anti-turbulence interface.

14. The system of claim 8, further comprising a mechanical device that sweeps the surface of he anti-turbulence interface to remove bubbles from the surface of the anti-turbulence interface.

15. The system of claim 1, wherein the at least one camera is a digital line-scan camera.

16. The system of claim 15, wherein the line-scan camera records one-dimensional lines and sends the one-dimensional lines to the digital processor.

17. The system of claim 1, wherein the digital processor sends a signal indicating the presence of a defect.

18. The system of claim 17, wherein the signal activates an alarm.

19. The system of claim 17, further comprising a separation mechanism that separates defective material, wherein the signal activates the separation mechanism.

20. The system of claim 17, wherein the signal activates an external control system that marks a batch in which a defect was detected.

21. The system of claim 1, further comprising a structure that holds the liquid bath, wherein the structure has a transparent wall, and wherein the at least one camera views the material through the transparent wall.

22. A system for detecting defects in material traveling through a liquid bath comprising:
 (a) a light that illuminates the material;
 (b) an anti-turbulence interface that has a surface in contact with the liquid bath;
 (c) a camera outside of the liquid bath that views the material through the surface; and
 (d) a digital processor in communication with the camera, wherein the digital processor receives image data from the camera and analyzes the image data to identify defects in the material, and wherein the digital processor is in communication with the light and is adapted to control the decree of illumination provided by the light to optimize the image data.

23. The system of claim 22, wherein the light comprises a light diffuser submerged in the liquid bath and a light source external to the liquid bath, wherein the light diffuser and the light source are in optical communication.

24. The system of claim 22, wherein the anti-turbulence interface is connected to the camera.

25. The system of claim 22, wherein the surface of the anti-turbulence interface is angled with respect to the general horizontal plane of the surface of the liquid bath.

26. The system of claim 22, wherein the anti-turbulence interface is a five-sided box having an open side, wherein the surface is opposite the open end, and wherein the five-sided box is partially submersed in the liquid bath with the open end facing up toward the camera.

27. The system of claim 22, wherein the surface of the anti-turbulence interface is coated with a coating that inhibits collection of gas molecules on the surface.

28. The system of claim 27, wherein the coating is hydrophilic.

29. The system of claim 22, further comprising a liquid injection mechanism that produces a flow of liquid across the surface of the anti-turbulence interface to remove bubbles from the surface of the anti-turbulence interface.

30. The system of claim 22, further comprising a vibration mechanism that vibrates the anti-turbulence interface to remove bubbles from the surface of the anti-turbulence interface.

31. The system of claim 22, further comprising a mechanical device that sweeps the surface of the anti-turbulence interface to remove bubbles from the surface of the anti-turbulence interface.

32. The system of claim 22, wherein the camera is a digital line-scan camera that records one-dimensional lines and sends the one-dimensional lines to the digital processor.

33. The system of claim 32, wherein the digital processor assembles the one-dimensional lines into a two-dimensional image, analyzes the two-dimensional image data for defects, and indicates the presence of a defect.

34. A method for detecting defects in a material comprising:
 conveying the material through a liquid bath;
 illuminating the material through the liquid bath;
 viewing the material through the liquid bath;
 capturing image data of the material;
 controlling the degree of illumination to optimize the image data; and
 identifying defects in the material from the image data.

35. The method of claim 34, wherein the material is one or more polymer strands.

36. The method of claim 34, wherein the liquid bath is held in a structure, wherein the structure has a transparent wall, and wherein viewing the material comprises viewing the material through the transparent wall.

37. The method of claim 34, wherein the liquid bath has a top surface, and wherein viewing the material comprises:
 placing an anti-turbulence interface in contact with the top surface of the liquid bath; and
 viewing the material through the anti-turbulence interface.

38. The method of claim 34, wherein viewing the material comprises submerging a camera in the liquid bath.

39. The method of claim 34, wherein capturing image data comprises:
 scanning one-dimensional lines of the material as the material passes in front of a line scan camera;
 sending the one-dimensional lines to a memory buffer in a digital processor; and
 assembling the one-dimensional lines into a two-dimensional image.

40. The method of claim 39, wherein identifying defects comprises identifying dark portions in the two-dimensional image that are indicative of a defect.

41. The method of claim 34, wherein identifying defects comprises:
  determining a non-defective material video level at which light passes through non-defective material;
  determining a defective material video level that indicates a defect in the material;
  establishing a threshold level between the non-defective material video level and the defective material video level; and
  identifying the defects as instances when a video level of the image data falls below the threshold level.

42. The method of claim 34, further comprising:
  associating the defects in the image data with portions of the material; and
  removing the portions from the material.

43. A system for detecting defects in a material comprising:
  means for conveying the material through a liquid bath;
  means for illuminating the material through the liquid bath;
  means for viewing the material through the liquid bath;
  means for capturing image data of the material; and
  means for identifying defects in the material from the image data,
    wherein the means for identifying defects is in communication with the means for illuminating and is adapted to control the degree of illumination provided by the means for illuminating to optimize the image data.

* * * * *